United States Patent [19]

Uematsu et al.

[11] Patent Number: 4,551,222
[45] Date of Patent: Nov. 5, 1985

[54] FLOW THROUGH SYSTEM LIQUID MEMBRANE TYPE ELECTRODE

[75] Inventors: Hiroaki Uematsu; Junji Aoki, both of Kyoto, Japan

[73] Assignee: Horiba, Ltd., Kyoto, Japan

[21] Appl. No.: 622,262

[22] Filed: Jun. 19, 1984

[30] Foreign Application Priority Data

Jun. 25, 1983 [JP] Japan .............................. 58-99728[U]

[51] Int. Cl.$^4$ ........................................... G01N 27/46
[52] U.S. Cl. .................................. 204/417; 204/416; 204/435
[58] Field of Search ................ 204/417, 435, 416, 418, 204/419, 1 T

[56] References Cited

U.S. PATENT DOCUMENTS

| | | |
|---|---|---|
| 3,467,590 | 9/1969 | Gibson et al. .................. 204/417 |
| 3,505,196 | 4/1970 | Dahms ............................: 204/435 |
| 3,591,482 | 7/1971 | Neff et al. ....................... 204/435 |
| 3,616,409 | 10/1971 | Tosteson ......................... 204/417 |
| 3,725,237 | 4/1973 | Matsuyama et al. .......... 204/417 |
| 4,135,999 | 1/1979 | Schindler et al. .............. 204/435 |
| 4,314,895 | 2/1982 | Spaziani et al. ................ 204/417 |

Primary Examiner—T. Tung
Attorney, Agent, or Firm—Wenderoth, Lind & Ponack

[57] ABSTRACT

A flow through system liquid membrane type electrode used for measuring a specific ion concentration in a flowing liquid sample. A cylindrical membrane holding member which is flat at one side surface, holds a sheet-like liquid membrane, the liquid membrane facing a liquid sample passage formed in a synthetic resin block, thereby to form a strong junction between the liquid membrane and the sample passage.

6 Claims, 4 Drawing Figures

FLOW THROUGH SYSTEM LIQUID MEMBRANE TYPE ELECTRODE

BACKGROUND OF THE INVENTION

1. Field of the Invention

This invention relates to an improved flow through system liquid membrane type electrode used for measuring a specific ion concentration in a liquid sample while the liquid sample is flowing.

2. Description of the Prior Art

FIG. 1 shows an example of a conventional flow through system liquid membrane type electrode, in which a liquid sample flow tube 13 extends through a housing 12 having a cover 11, a communicating bore 14 is formed at the liquid sample flow tube 13, a liquid membrane 15 is connected to the bore 14, an internal electrode 16 is mounted at a predetermined portion of housing 12, and an internal liquid 17 is enclosed in the housing 12. Such a conventional electrode is superior in handling and provides in its flow tube 13 a liquid sample passage D, thereby being advantageous in that its assembly in liquid flow lines is simple and easy.

The smaller the diameter of passage D in the liquid sample flow tube 13, the more suitable the tube 13 for measuring a constituent in a very small sample, and the smaller the outer diameter of the liquid sample flow tube 13, the more compact the electrode as a whole. Hence, a tube smaller in diameter and thickness has hitherto been used as the liquid sample flow tube 13.

Therefore, the conventional electrode is extremely small in an area of junction between the liquid membrane and the communicating bore 14. Moreover, the face of the junction is curved and therefore difficult to join. Also, since the flow tube 13 is small in diameter, it has reduced strength. It is not possible to intensively urge the liquid membrane 15 against the bore so that it is strongly held thereto. As a result, the strength of the junction between liquid membrane 15 and bore 14 is quite low.

SUMMARY OF THE INVENTION

An object of the invention is to provide a flow through system liquid membrane type electrode having a simple modification which raises the junction strength of the liquid membrane so as to eliminate the defect in the conventional construction without negating the advantage of the conventional construction. The flow through system liquid membrane type electrode of the invention attains this object by providing a synthetic resin block having a space containing therein an internal electrode and an internal liquid, a passage for a liquid sample, and a cylindrical communicating space through which the liquid sample passage communicates with the internal liquid containing space. A cylindrical membrane holding member is provided in contact with a liquid membrane on a single flat surface at one side so as to face the liquid sample passage. A lid is provided for keeping the internal liquid in a sealed condition.

The electrode of the invention is superior in handling and ease of assembly with respect to connection to the liquid flow line as is the conventional one, and also is provided especially with the membrane holding member such that the liquid membrane is joined thereto in only one plane, thereby enabling the junction strength of the liquid membrane to be extremely high. By providing the face of the junction in only one plane, the area of the junction of the liquid membrane can be enlarged regardless of the diameter of the liquid sample passage, and the membrane holding member is made strong enough to withstand the pressure applied thereto, whereby a junction strength much stronger than the conventional one is obtainable. Moreover, in spite of the larger junction area, the liquid sample passage is reducible in diameter, thereby being suitable for measuring the constituents of a trace amount of liquid sample. Therefore, the flow through system liquid membrane type electrode of the invention, as a whole, while retaining the advantages of the conventional one, has remarkably improved junction strength at the liquid membrane.

In a preferred embodiment of the invention, the boundry of the liquid sample passage is U-shaped in cross-section only at the portion communicating with the communicating space and is cylindrical at the other portions thereof. Thus, the area of the liquid membrane contacting the liquid sample can be enlarged while the liquid sample passage is basically cylindrical in cross section so as to facilitate manufacture.

Furthermore, an opening in the membrane holding member which provides communication between the liquid membrane and the interior liquid is formed in an elongate slot coincident with the portion of the liquid sample passage having a U-shaped boundary to greatly enlarge the area of liquid membrane thereby facilitating improvement of measuring accuracy.

BRIEF DESCRIPTION OF THE DRAWINGS

These and other aspects of the invention will become more apparent in the detailed description and examples which follow, when taken in conjunction with the accompanying drawings in which.

DESCRIPTION OF THE PREFERRED EMBODIMENT

Figure 1:
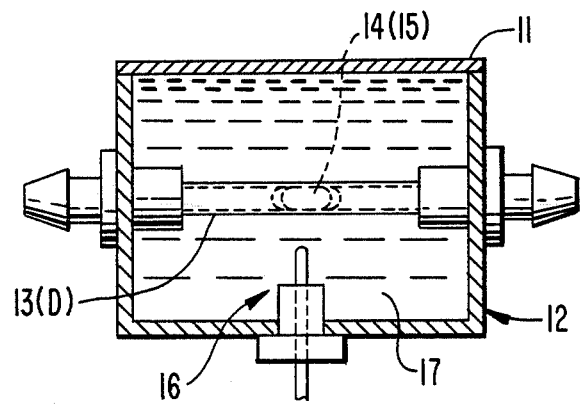
FIG. 1 is a sectional view exemplary of a conventional flow through system liquid membrane type electrode.
Figure 2:
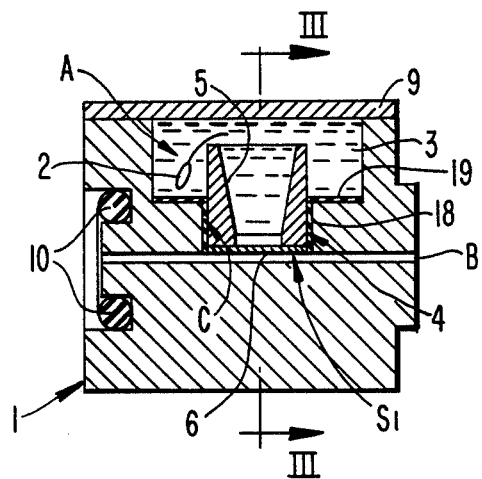
FIG. 2 is a longitudinal section side view of a flow through system liquid membrane type electrode in accordance with an embodiment of the invention.
Figure 3:
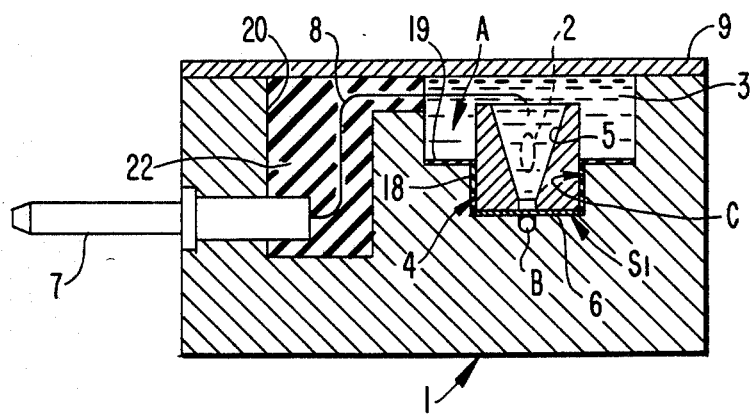
FIG. 3 is a longitudinal sectional view taken on line III—III in FIG. 2.
Figure 4:
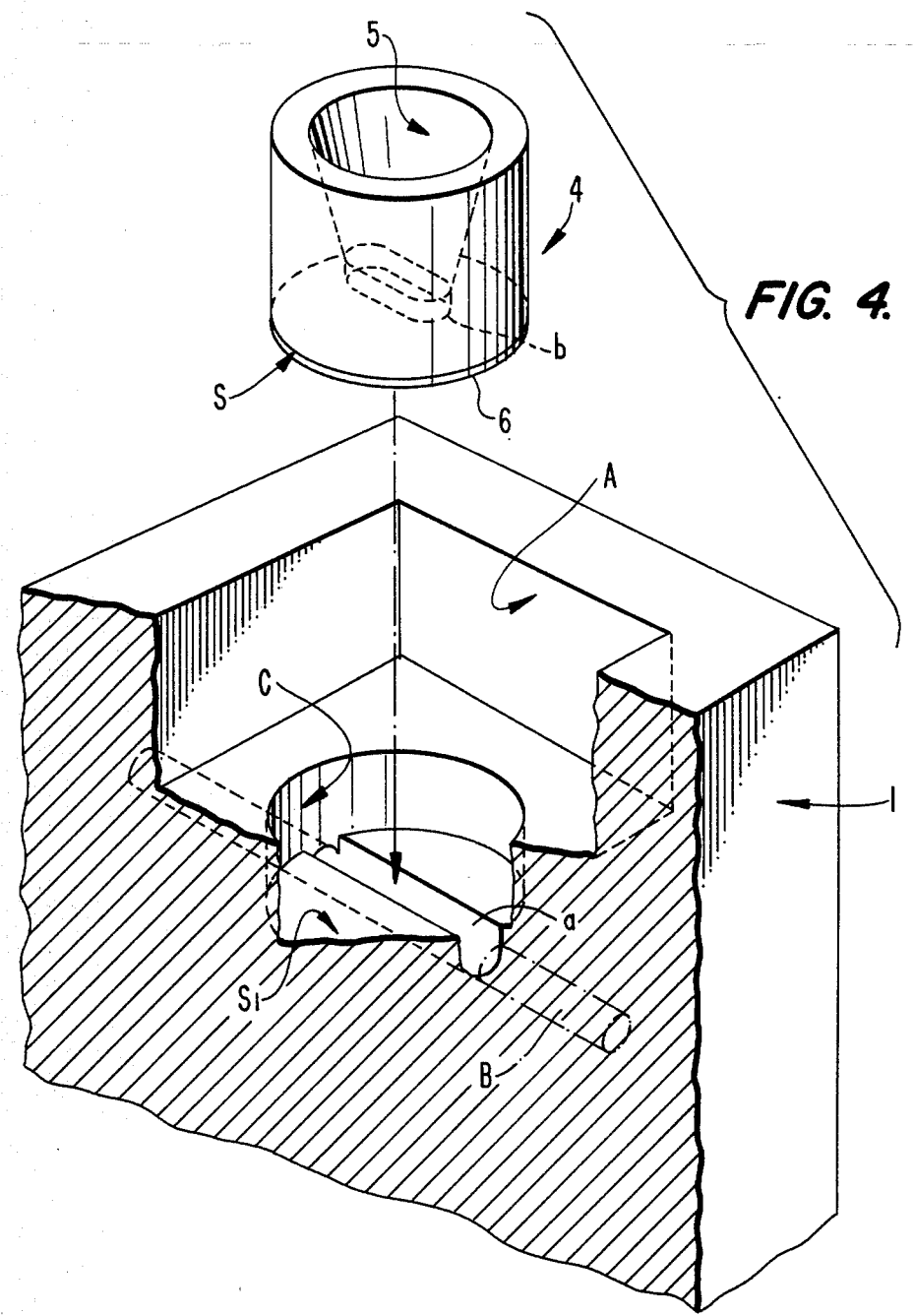
FIG. 4 is an exploded perspective view of a block and a membrane holding member in accordance with the invention.

Referring to FIGS. 2-4, reference numeral 1 designates a body block made of transparent synthetic resin such as acrylic acid resin which has formed therein a space A for containing therein an internal electrode 2 and an internal liquid (inner solution) 3, that is electrolyte solution such as KCl, a liquid sample passage B of smaller diameter which extends straight and horizontally through block 1, and a generally cylindrical communicating space C through which the liquid sample passage B communicates with the space A.

Since the block 1 is made of transparent synthetic resin, visual supervision of flowing condition of the liquid can be done with ease.

Referring in detail to FIG. 4, the cylindrical space C has a circular flat base surface $S_1$. Part of liquid sample passage B which communicates with the cylindrical portion C, has a boundary which opens upward into surface S, and therefore is U-shaped in cross section and is larger than other portions of passage B which are circular in cross section, the base of the boundary of the U-shaped portion being continuous to the base of the other portions.

Reference numeral 4 designates a cylindrical membrane holding member having a flat bottom face S, which has an elongated slot b in face S facing and coincident with the open end a of the U-shaped portion of passage B in cylindrical space C and which has a bore 5 tapered downwardly and communicating with the slot b. To the flat face S covering the slot b is applied a liquid membrane 6 which is disclosed in Japanese Patent Application Laid Open Number 55-43488.

The membrane holding member 4 is mounted in the cylindrical space C in the block 1 so as to bring the liquid membrane 6 into pressing contact with the flat face $S_1$ at the bottom of the cylindrical communicating space C. In this position, liquid membrane 6 faces the liquid sample passage B, thereby closing off the base of the cylindrical space C from liquid passage B. The cylindrical side walls of membrane holding member 4 are electrically insulated from the block 1 by a cylindrical layer of resin material 18 such as silicon. The bottom surface of the space A is also covered with a layer of insulating resin material 19 such as silicon.

A connector pin 7 extends through a side of block 1 into a cavity 20 adjacent space A. A lead wire 8 passing through cavity 20 connects pin 7 to internal electrode 2. Lead wire 8 is insulated from block 1 by a filler 22 made of resin material such as silicon which fills cavity 20.

Reference numeral 9 designates a lid for enclosing the internal liquid 3 in space A and reference numeral 10 designates an O-ring provided in a recessed ring-shaped groove in a side wall of block 1 so as to surround liquid passage B.

The slot b can alternatively be formed with other shapes for improving the measuring accuracy of the device.

While a preferred embodiment of the invention has been described in detail above, such description is for illustrative purposes only, and it is to be understood that changes and variations may be made without departing from the spirit and scope of the invention which is defined only by the following claims.

What is claimed is:

1. An electrode, comprising:
   a synthetic resin block having a liquid containing space formed therein;
   an internal liquid contained in said liquid containing space;
   an internal electrode contained in said liquid containing space immersed in said liquid;
   a straight line sample passage extending entirely and straight through said block for carrying liquid therethrough, having a continuous straight boundary surface portion extending entirely through said block and consisting of two cylindrical first sections having uniform equal diameters and a second section between said two first sections;
   a communicating space connecting said sample passage and said liquid containing space having a flat planar interior surface, said second section of said sample passage extending along said interior surface and having an outer periphery having a uniform, smooth, concavely arched cross section such that the furthest point in said cross section of said second portion from the plane of said planar interior surface is a distance from said plane equal to said diameter of said first sections;
   a cylindrical membrane holding member fitted in said communicating space;
   a liquid membrane member held between said sample passage and said communicating space such that said liquid membrane member faces said sample passage, blocking communication between said sample passage and said liquid; and
   a lid covering said liquid containing space so that said lid and said block enclose said internal liquid.

2. An electrode as in claim 1, wherein said cylindrical membrane holding member has a holding member passage therein providing communication between said liquid membrane member and said internal liquid, said holding member passage terminating at one end at said liquid membrane member and with an elongated slot coincident with said second portion of said sample passage.

3. An electrode as in claim 2 wherein said holding member passage includes a conical bore converging from said liquid containing space to said elongated slot.

4. An electrode as in claim 3, wherein said resin block is transparent.

5. An electrode as in claim 1, wherein said straight boundary surface is semicircular in cross section, said furthest point being located at the center of the semicircular arc defined thereby.

6. An electrode as in claim 1, wherein said block is substantially box shaped, and rectangular in cross section.

* * * * *